(12) United States Patent
Wilson

(10) Patent No.: US 11,745,230 B2
(45) Date of Patent: *Sep. 5, 2023

(54) CLEANING APPARATUS

(71) Applicant: Jerome Wilson, Blanchester, OH (US)

(72) Inventor: Jerome Wilson, Blanchester, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/185,310

(22) Filed: Mar. 16, 2023

(65) Prior Publication Data

US 2023/0226580 A1   Jul. 20, 2023

Related U.S. Application Data

(63) Continuation of application No. 16/833,926, filed on Mar. 30, 2020, now Pat. No. 11,607,717.

(51) Int. Cl.
*B08B 9/027* (2006.01)
*B08B 9/023* (2006.01)
*A61M 16/08* (2006.01)

(52) U.S. Cl.
CPC .............. *B08B 9/027* (2013.01); *B08B 9/023* (2013.01); *A61M 16/0875* (2013.01); *A61M 2209/10* (2013.01); *B08B 2209/027* (2013.01)

(58) Field of Classification Search
CPC ........... B08B 9/22; B08B 9/023; B08B 9/027; B08B 9/00–46; B08B 3/04; B08B 3/048; B08B 3/08; B08B 3/00–14; A61B 1/126; A61B 90/70; A61B 2090/701; A61M 16/0875; A61M 16/00–22; A61M 39/00; A61M 39/08; B01L 13/00; B01L 13/02; A47L 15/00–508

See application file for complete search history.

(56) References Cited

FOREIGN PATENT DOCUMENTS

| DE | 3443912 A1 | * | 6/1986 |
| DE | 3710349 A1 | * | 10/1988 |
| EP | 0452790 A1 | * | 10/1991 |

* cited by examiner

*Primary Examiner* — Mikhail Kornakov
*Assistant Examiner* — Richard Z. Zhang
(74) *Attorney, Agent, or Firm* — Jenei LLC

(57) ABSTRACT

A cleaning apparatus for cleaning of medical machine components of machines such as CPAP machines, nebulizers, PEEP machines, and the like is disclosed herein. The cleaning apparatus comprises a container body. A carousel is configured for placement within the container body. The carousel comprises a support structure. The carousel further comprises a helical ramp attached to the support structure and extending helically from an operative top end of the support structure to an operative bottom end of the support structure along a periphery of the support structure.

5 Claims, 4 Drawing Sheets

CLEANING APPARATUS

CROSS-REFERENCE TO RELATED APPLICATIONS

The present Application is a continuation of U.S. patent application Ser. No. 16/833,926 entitled "CLEANING APPARATUS", filed Mar. 30, 2020, which is hereby expressly incorporated by reference herein for all purposes.

TECHNICAL FIELD

The present disclosure relates generally to a cleaning apparatus, and more particularly, to a cleaning apparatus for cleaning different components of different medical machines, e.g., a continuous positive airway pressure (CPAP) machine.

BACKGROUND OF THE INVENTION

Sleep apnea is a sleep-associated disorder in which a person has momentary breaks in breathing or periods of shallow breathing during sleep. Each such break can last for a few seconds to a few minutes, and usually occur many times in a night. In the most common form of sleep apnea, each such break in the breathing is followed by loud snoring, subsequent to which there may be a choking or a snorting sound when the breathing resumes.

Sleep apnea is of two types. The first type of sleep apnea is central sleep apnea (CSA) in which the breathing repeatedly stops and starts during sleep. CSA occurs because the brain does not send proper signals to the muscles that control the breathing. The second type sleep apnea is obstructive sleep apnea (OSA). In OSA, the breathing of a person is interrupted because of a blockage to the airflow. A person may either have CSA or OSA or both. OSA is the most commonly occurring form of sleep apnea. Some people with sleep apnea are unaware they have the condition. Sleep apnea disrupts sleep cycle, which may cause a person to experience sleepiness or feel tired during the day.

To this end, different methods for treating or at least mitigating the effects sleep apnea are developed in the art. One such method involves usage of nose clips, wherein the nose clips are designed to prevent the closing of the nasal airway gap. By preventing the closing of the nasal airway gap, OSA can be prevented.

Another widely used method for dealing with sleep apnea involves the usage of a continuous positive airway pressure (CPAP) machine. The CPAP machine gently blows pressurized air through a user's airway at a constant pressure that keeps the throat from collapsing. The CPAP machine typically includes a CPAP motor, a CPAP mask, and a hose. The hose facilitates the air communication between the CPAP motor and the CPAP mask. The CPAP mask and the CPAP hose are exposed to nasal and oral secretions and often require frequent cleaning for maintenance of optimal hygiene. However, it is difficult to properly clean the hose because when the hose is dipped into water or a cleaning solution, the air is trapped inside the hose which prevents the hose from properly sinking into the cleaning solution. When the hose does not sink into the cleaning solution, an optimal contact between the surfaces of the hose and the cleaning solution is not achieved. As such, the hose is not cleaned properly, which is not desired.

Accordingly, there is felt a need of a cleaning apparatus that can be used for optimally cleaning different components of the medical machines such as CPAP machine, nebulizers, and the like.

SUMMARY OF THE INVENTION

The present disclosure provides a cleaning apparatus. The cleaning apparatus comprises a container body. A carousel is configured for placement within the container body. The carousel comprises a support structure conforming with the shape of the container body. The carousel further comprises a helical ramp attached to the support structure and extending helically from an operative top end of the support structure to an operative bottom end of the support structure along a periphery of the support structure.

The above summary contains simplifications, generalizations and omissions of detail and is not intended as a comprehensive description of the claimed subject matter but, rather, is intended to provide a brief overview of some of the functionality associated therewith. Other systems, methods, functionality, features and advantages of the claimed subject matter will be or will become apparent to one with skill in the art upon examination of the following figures and detailed written description.

BRIEF DESCRIPTION OF THE DRAWINGS

The description of the illustrative embodiments can be read in conjunction with the accompanying figures. It will be appreciated that for simplicity and clarity of illustration, elements illustrated in the figures have not necessarily been drawn to scale. For example, the dimensions of some of the elements are exaggerated relative to other elements. Embodiments incorporating teachings of the present disclosure are shown and described with respect to the figures presented herein, in which.

DETAILED DESCRIPTION OF EXAMPLE EMBODIMENTS

Medical machines such as CPAP machine, nebulizers, and Positive end-expiratory pressure (PEEP) machines, and the like involve the usage of hoses, masks, and the like. The hoses and masks of some of these machines are exposed to nasal and oral secretions of the user. Maintaining cleanliness of these components is desired because unclean components may become a cause of infections. Conventionally, these components are cleaned by soaking them in water or a cleaning solution. However, hoses tend to float on the water or the cleaning solution because the air trapped inside the hose prevents the hose from sinking into the cleaning solution. This is not desired.

To this end, the present disclosure envisages a cleaning apparatus for cleaning of different components of CPAP machines, nebulizers, and PEEP machines. The cleaning apparatus, in accordance with an embodiment of the present disclosure, comprises a container body and a carousel configured for placement within the container body. The carousel has a construction that allows a user to support a hose securely on the carousel. The carousel can then be disposed within the container body and locked in place within the container body while securely holing the hose in place. The hose is held within the container by the carousel such that when the carousel is fitted in the container body, the hose is held and immersed inside the cleaning solution that is present in the container body. Since, the hose is held by the carousel, the air trapped inside the hose escapes in the form of air bubbles through the cleaning solution that is present in the container body. As such, the entire surface area of the hose is in contact with the cleaning solution to ensure that the hose is optimally clean for the next usage.

Figure 1:
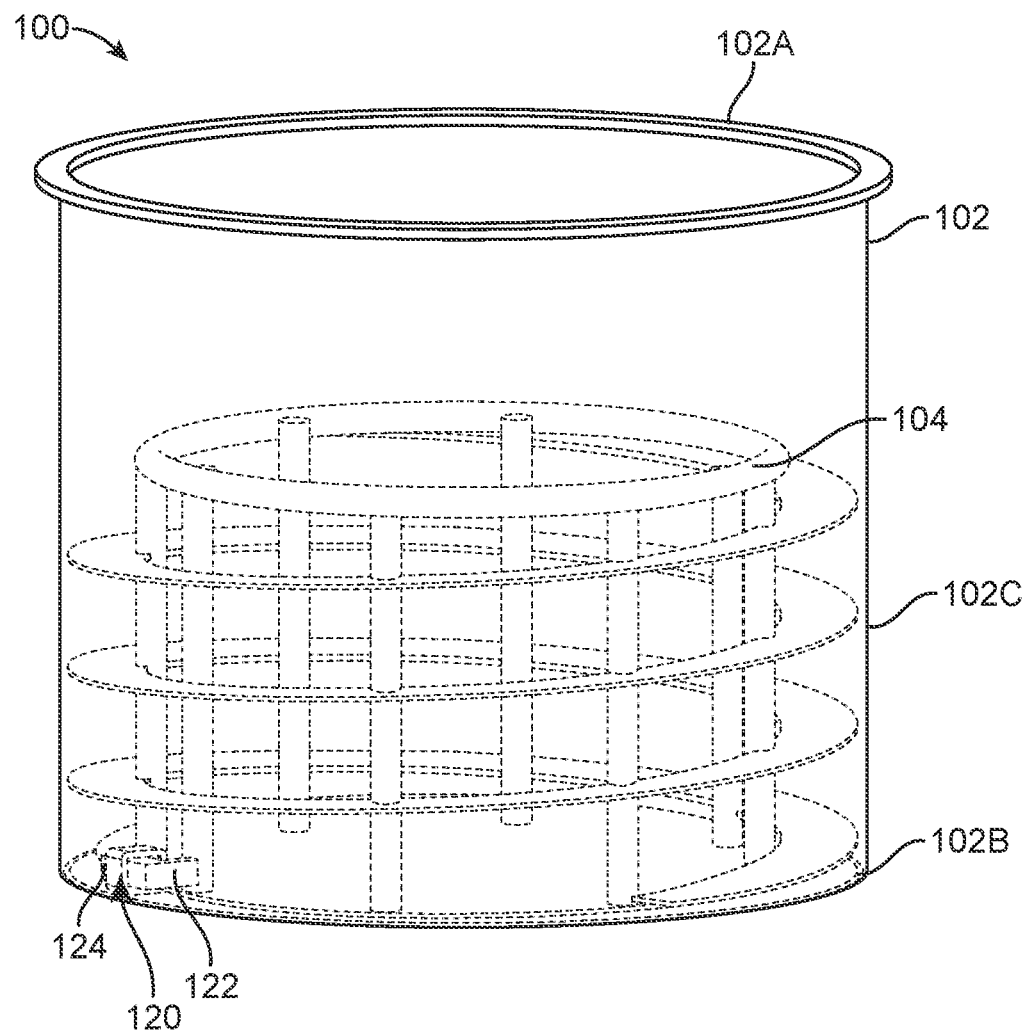
FIG. 1 illustrates an isometric view of cleaning apparatus, according to one or more embodiments.

A cleaning apparatus 100, in accordance with an embodiment of the present disclosure, is hereinafter described with reference to FIG. 1 thru FIG. 3. The cleaning apparatus 100 (hereinafter referred to as apparatus 100) comprises a container body 102. The container body 102 has an operative top end 102A, an operative bottom end 102B and an operative side 102C. The container body 102, as seen in FIG. 1, has a cylindrical shape. However, the container body 102 is not limited to have a cylindrical configuration and can also have a square configuration, a rectangular configuration, an elliptical configuration, and the like.

In one or more embodiments, the container body 102 may have conical sides 102C wherein the operative bottom end 102B is smaller than the operative top end 102A, particularly to allow for stacking of multiple container bodies 102. In one or more additional embodiments, the operative top end 102A of the container body 102 may comprise a lid (not shown).

Figure 2:
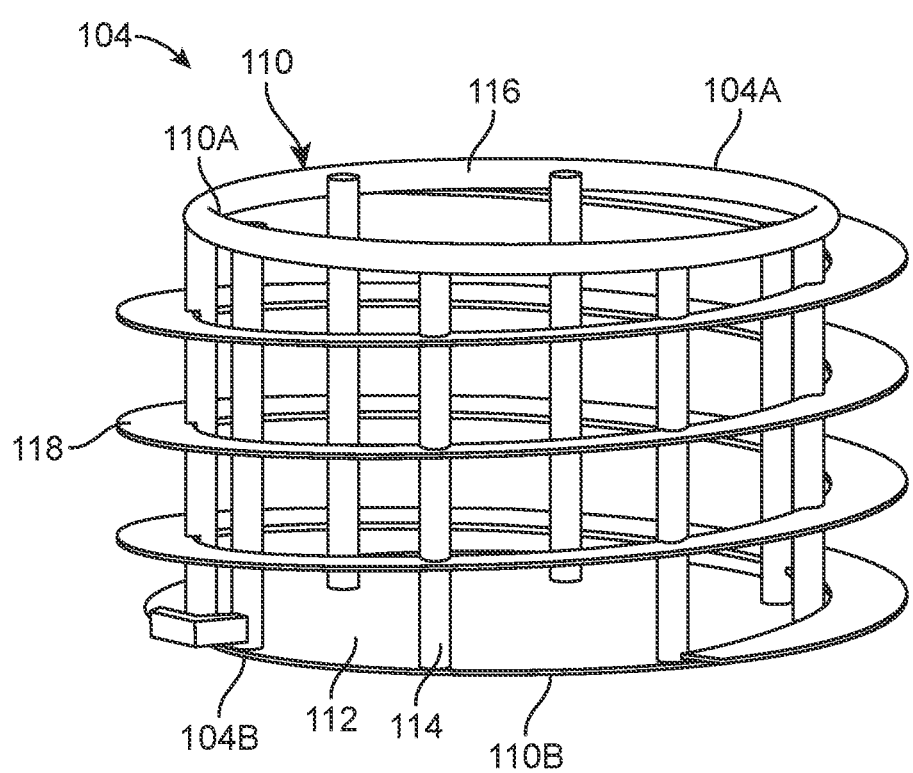
FIG. 2 illustrates an isometric view of a carousel used in the cleaning apparatus, according to one or more embodiments.

The apparatus 100 further comprises a carousel 104, which is separately illustrated in FIG. 2. The carousel 104 has an operative top end 104A and an operative bottom end 104B. The carousel 104 is the component of the apparatus 100 that is designed to securely hold a hose 106 (shown in FIG. 3) immersed within a cleaning solution 108 present within the container body 102. More specifically, the carousel 104 prevents the hose 106 to float on top of the cleaning solution 108 by completely immersing the hose 106 within the cleaning solution 108 and holding the hose 106 in that immersed position. The air trapped within the hose 106 escapes from the hose 106 in the form of air bubbles through the cleaning solution 108 when the hose 106 is completely immersed or dipped in the cleaning solution 108. As such, the cleaning solution 108 is in contact with the entire surface area of the hose 106, which facilitates optimal cleaning of the hose 106.

The cleaning solution 108 may be of various types and may vary according to need. Accordingly, there is no best fluid to be provided. In one or more embodiments, the cleaning solution 108 comprises water, a mild soap solution, a vinegar solution or any suitable cleaning and disinfecting composition. Typically, the cleaning fluid has the composition of soap, vinegar and water solution in the ratio of one-part soap, one-part vinegar and twenty-parts water. A low phosphoric soap is preferred so as to be less toxic to the environment. Of course, the cleaning fluid in accordance with the instant invention is non-toxic and safe as a cleaning fluid for human usage.

The carousel 104 further comprises a support structure 110, in accordance with one embodiment of the present disclosure. In one or more embodiments, the support structure 110 comprises a base 112, wherein the base 112 is a plate-like component having a shape conforming with the cross section of the container body 102. In another embodiment, the base 112 is an opening in the support structure 110.

It is to be noted that the shape of the base 112 may also be different from the shape of the container body cross section. For example, the base 112 may have a circular shape and can be placed inside a container body having a rectangular cross-section. Alternatively, the base 112 is not limited to being circular and may have any shape corresponding to the cross-section of the container body 102. In the present embodiment illustrated in FIG. 3, the base 112 has a circular shape.

The support structure 110 further comprises a plurality of support pillars 114 supported on the base 112 arranged along the periphery of the base 112. As seen in the exemplary embodiment illustrated FIG. 1 thru FIG. 4, the base 112 has a circular shape, and the support pillars 114 of the support structure 110 are arranged in a spaced apart configuration to define a cylindrical array of support pillars 114 on the base 112 along the periphery of the base 112.

The operative top ends of the support pillars 114 are terminated into a top element 116. The top element 116, as seen in FIG. 1 thru FIG. 3 is a ring. However, the top element 114 is not limited to being a ring and may have a shape corresponding to the shape of the base 112. The top element 116, the support pillars 114, and the base 112 form the support structure 110. Such a construction of the support structure 110 including the top element 116, the support pillars 114, and the base 112 is compact and sturdy.

The carousel 104 further comprises a helical ramp 118. The helical ramp 118 is attached to the support structure 110, and more specifically, to the support pillars 114. The helical ramp 118 extends helically from an operative top end 110A to an operative bottom end 110B of the support structure 110 along a periphery thereof. The helical ramp 118, as seen in FIG. 3, securely holds the hose 106 in place. More specifically, the hose 106 is placed onto the helical ramp 118 and immersed into the cleaning solution 108, while the carousel 104 is locked into place within the container body 102. The locking of the carousel 104 within the container body 102 restricts any upward movement of the hose 106 caused due to the entrapment of air within the hose 106, as the hose 106 simply abuts the helical ramp 118 when the carousel 104 and the 106 are immersed within the cleaning solution 108 and locked in place within the container body 102.

In one or more embodiment, the locking of the carousel 104 within the container body 102 is facilitated by an optional locking arrangement 120. As illustrated in FIG. 1 thru FIG. 3, the locking arrangement 120 comprises an L-shaped protrusion 122 configured adjacent an operative bottom end 104B of the carousel 104. The locking arrangement 120 further comprises a receiving protrusion 124 configured on an operative bottom end 102B of the container body 102. For locking the carousel 104 within the container body 102, the carousel 104 is inserted within the container body 102 and rotated until the L-shaped protrusion 122 is inserted within or received within the receiving protrusion 124. In another embodiment, the positions of the L-shaped protrusion 122 and the receiving protrusion 124 may be swapped with the receiving protrusion configured on the carousel and the L-shaped protrusion configured on the container body.

Figure 3:
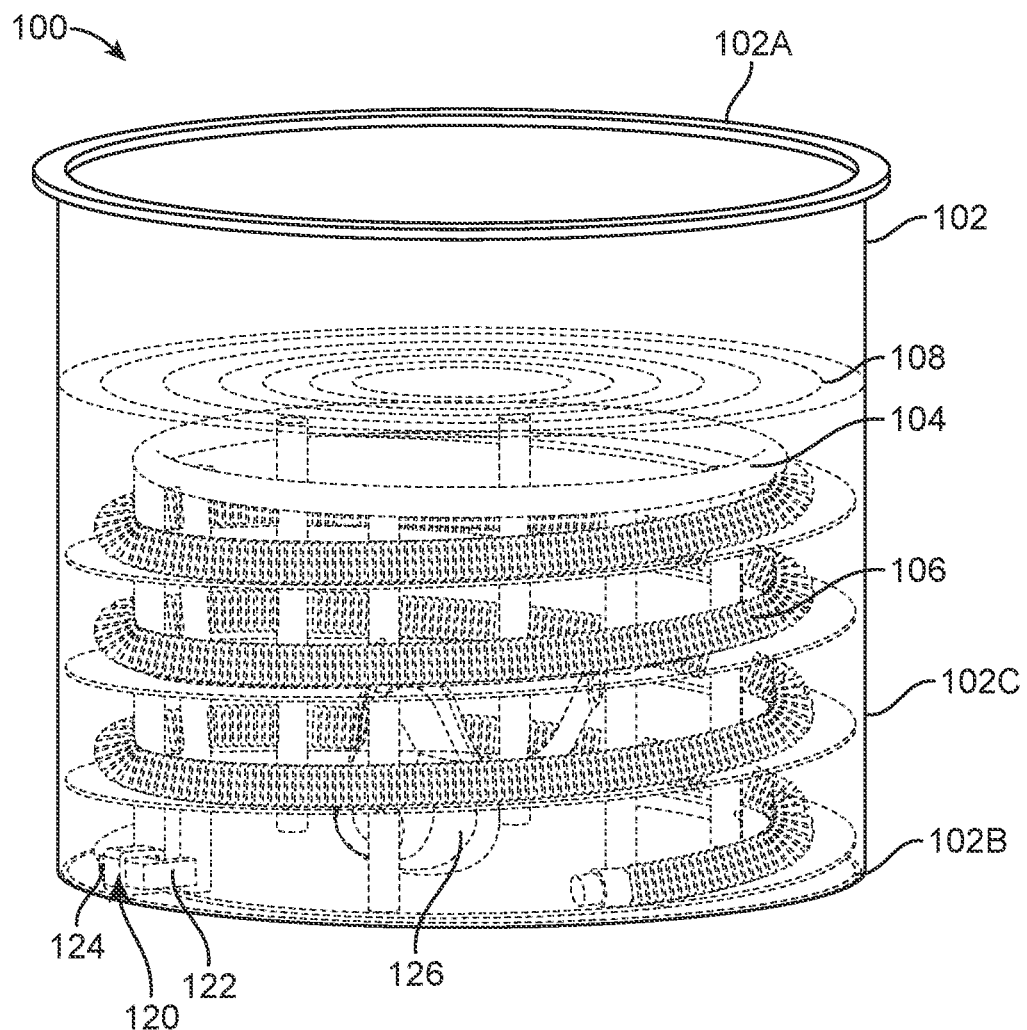
FIG. 3 illustrates another isometric view of cleaning apparatus, according to one or more embodiments.

While the hose 106 is supported in the container body 102 on the carousel 104 adjacent the inner periphery of the container body 102, the central area of the container body 102 may be used to clean the other components, e.g., a mask 126 or water chamber (not shown), as can be seen in FIG. 3. The cleaning solution 108 may be water or a mixture of water and a cleaning agent.

In one embodiment, the elements of the carousel 104, i.e., the support structure 110 and the helical ramp 118, are integral and manufactured via molding operation in a single mold. In one embodiment, the carousel 104 may be made of a plastic material. In another embodiment, the carousel 104 may be made of a corrosion resistant metallic material.

Figure 4:
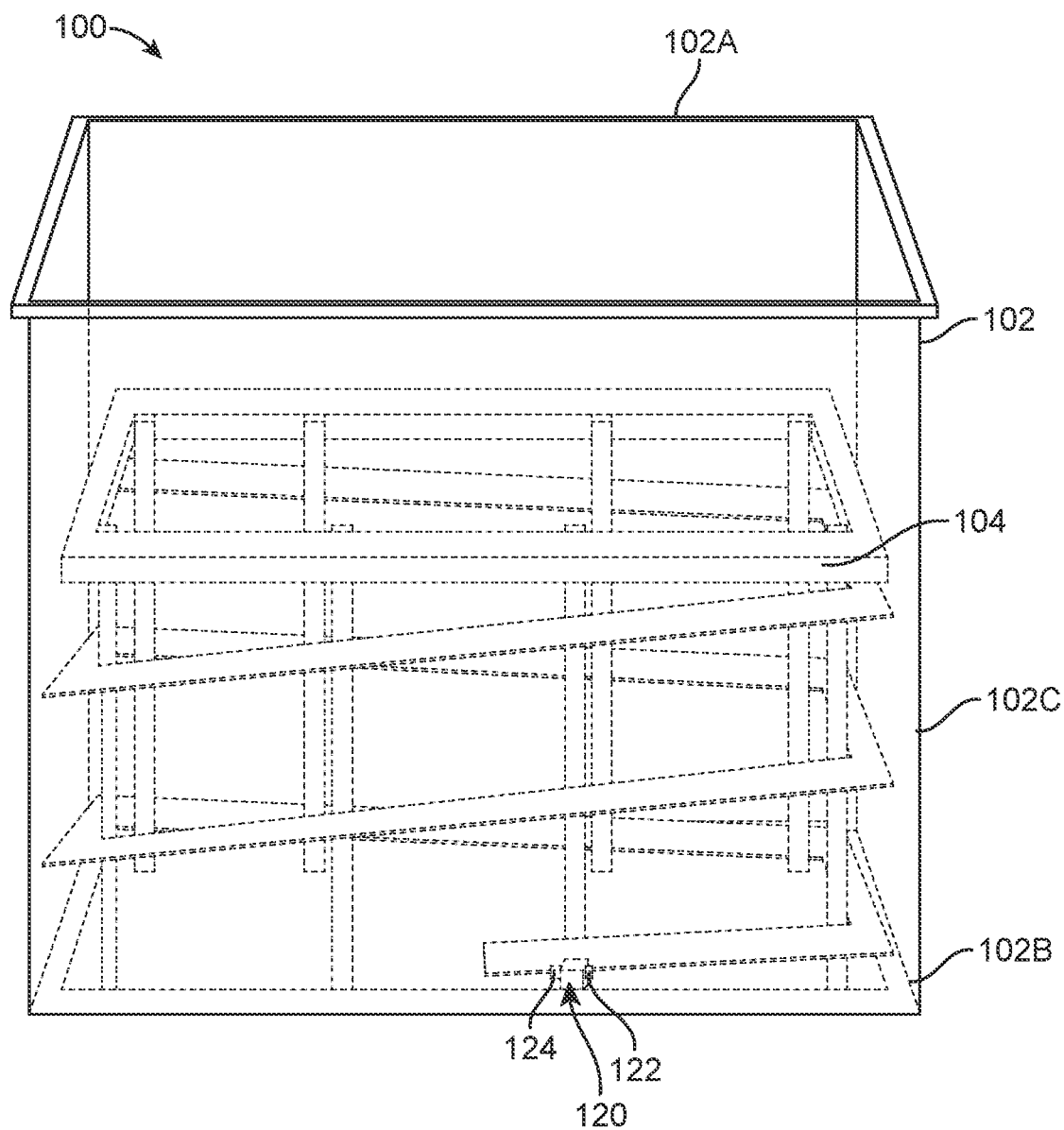
FIG. 4 illustrates an isometric view of cleaning apparatus, according to one or more embodiments.

FIG. 4 illustrates an isometric view of an alternative embodiment of the apparatus 100. Referring to FIG. 4, the container body 102 and the carousel 104 have a rectangular shape. It is to be noted that container body 102 and the carousel 104 may have any other shape as well and are not limited to being either circular or rectangular.

An advantageous aspect of the apparatus 100 is the ability to facilitate cleaning of the hose 106 and the mask 126 in a manner that is very convenient and easy to the user. More specifically, as against the conventional method of cleaning the hose where the hose repeatedly floats on top of the cleaning solution, using the apparatus 100, the user does not need to worry about optimal contact establishment between the cleaning solution and the inner surface of the hose 106, which may be exposed disease causing viruses and bacteria present in nasal and oral secretions of the user.

While the disclosure has been described with reference to exemplary embodiments, it will be understood by those skilled in the art that various changes may be made, and equivalents may be substituted for elements thereof, without departing from the scope of the disclosure. In addition, many modifications may be made to adapt a particular system, device or component thereof to the teachings of the disclosure without departing from the essential scope thereof. Therefore, it is intended that the disclosure not be limited to the particular embodiments disclosed for carrying out this disclosure, but that the disclosure will include all embodiments falling within the scope of the appended claims. Moreover, the use of the terms first, second, etc. do not denote any order or importance, but rather the terms first, second, etc. are used to distinguish one element from another.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The description of the present disclosure has been presented for purposes of illustration and description but is not intended to be exhaustive or limited to the disclosure in the form disclosed. Many modifications and variations will be apparent to those of ordinary skill in the art without departing from the scope of the disclosure. The described embodiments were chosen and described in order to best explain the principles of the disclosure and the practical application, and to enable others of ordinary skill in the art to understand the disclosure for various embodiments with various modifications as are suited to the particular use contemplated.

What is claimed is:

1. An apparatus for cleaning a continuous positive airway pressure (CPAP) machine airway hose comprising:
    a container body having sidewalls, an open top end, and a closed bottom end, defining an interior space for containing a volume of a cleaning solution;
    a continuous positive airway pressure (CPAP) machine airway hose; and
    a carousel configured for placement within the container body the carousel comprising:
        a support structure having an operative top end and operative bottom end; and
        a helical ramp having a top surface and a bottom surface attached to the support structure and extending helically as loops in a circumferential direction at a pitch angle from the operative top end of the support structure to the operative bottom end of the support structure along a periphery of the support structure, thereby the hose is held within the container body by the carousel such that when the carousel is fitted in the container body, and the hose is held and immersed inside the cleaning solution filled in the container body, wherein air trapped inside the hose escapes in the form of air bubbles through the cleaning solution filled in the container body, such that the entire surface area of the hose is in contact with the cleaning solution to ensure that the hose is optimally clean.

2. The apparatus according to claim 1, further comprising a locking arrangement for locking the carousel within the container body, wherein the locking arrangement comprises:
    an L-shaped protrusion placed on one of the carousel and the container body at a location adjacent an operative bottom end belonging to said one of the carousel and the container body;
    a receiving protrusion placed on the other one of the carousel and the container body at a location adjacent an operative bottom end belonging to said other one of the carousel and the container body; and
    wherein the locking arrangement is actuated by rotating the carousel within the container body.

3. The apparatus according to claim 1, wherein the support structure comprises a base.

4. The apparatus according to claim 1, further comprising a lid.

5. The apparatus according to claim 1, further comprising the volume of the cleaning solution sufficient to partially fill the container body.

* * * * *